United States Patent [19]
Omura et al.

[11] Patent Number: 5,869,675
[45] Date of Patent: Feb. 9, 1999

[54] LACTACYSTIN DERIVATIVES

[75] Inventors: Satoshi Omura; Toshiaki Sunazuka; Haruo Tanaka, all of Tokyo, Japan

[73] Assignee: The Kitasato Institute, Tokyo, Japan

[21] Appl. No.: 979,637

[22] Filed: Nov. 28, 1997

Related U.S. Application Data

[63] Continuation of Ser. No. 579,340, Dec. 27, 1995, abandoned.

[30] Foreign Application Priority Data

Dec. 27, 1994 [JP] Japan .................................. 6-324465

[51] Int. Cl.$^6$ ...................... C07D 207/12; C07D 401/12
[52] U.S. Cl. ...................... 546/278.7; 548/530; 548/534
[58] Field of Search ...................... 548/530, 534; 546/278.7

[56] References Cited

FOREIGN PATENT DOCUMENTS 3-98594  4/1991  Japan .

OTHER PUBLICATIONS

Nagamitsu et al., "Structure–Activity Relationships of Lactacystin, the First Non–Protein Neurotrophic Factor", *The Journal of Antibiotics*, vol. 48, No. 7, 1995, pp. 747 and 748.
Corey et al., "An Enantioselective Synthesis of (6R)–Lactacystin", *Tetrahedron Letters*, vol. 34, No. 44, 1993, pp. 6969–6972.
Corey et al., Synthesis of (6R, 7S)–Lactacystin and 6–Deoxylactacystin from a Common Intermediate, *Tetrahedron Letters*, vol. 34, No. 44, 1993, pp. 6973–6976.
Corey et al., "Studies of the Total Synthesis of Lactacystin, and Improved Aldol Coupling Reaction and a β–Lactone Intermediate in Thiol Ester Formation", *Tetrahedron Letters*, vol. 34, No. 44, 1993, pp. 6977–6980.
Fenteany et al., "Inhibition of Proteasome Activities and Subunit–Specific Amino–Terminal Threonine Modification by Lactacystin", *Science*, vol. 268, 1995, pp. 726–731.
Fenteany et al., "A β–Lactone Related to Lactacystin Induces Neurite Outgrowth in a Neuroblastoma Cell Line and Inhibits Cell Cycle Progression in an Osteosarcoma Cell Line", *Proc. Natl. Acad. Sci. USA*, vol. 91, Apr. 1994, pp. 3358–3362.
*The Journal of Antibiotics*, vol. 44, No. 1, 1991, pp. 113–116.
G. Fenteany et al., "A β–lactone related to lactacystin induces neurite outgrowth in a neuroblastoma cell line and inhibits cell cycle progression in an osteosarcoma cell line", *Proc. Natl. Acad. Sci.*.
Corey et al., J. Am. Chem. Soc., 1992, 114, 10677–78.
Corey et al., Tetrahedron Letters, 1993, 34(44), 6969–72.
Corey et al., Tetrahedron Letters, 1993, 34(44), 6973–76.
Corey et al., Tetrahedron Letters, 1993, 34(44), 6977–80.
Nagamitsu et al., J. Am. Chem. Soc., 1996, 118, 3584–90.
Oomura et al., Chemical Abstracts, 115:134195u (1991).
Sunazuka et al., J. Am. Chem. Soc., 1993, 115, 5302.
Uno et al., J. Am. Chem. Soc., 1994, 116, 2139–40.

*Primary Examiner*—Fiona T. Powers
*Attorney, Agent, or Firm*—Young & Thompson

[57] ABSTRACT

Novel lactacystin derivatives other than lactacystin per se, with superior activity for the genesis of neurites and highly selective toxicity and low cytotoxicity as compared with known lactacystin have been prepared, of the formula

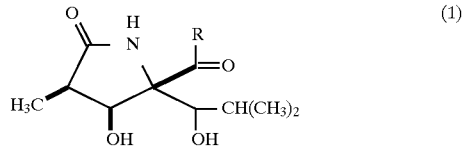

(1)

wherein R is lower alkoxy, $-S-(CH_2)_n R^1$ or $-S-(CH_2)_n-CH(R^2)-(R^3)$, in which $R^1$ is branched or straight-chain lower alkyl, hydroxy, carboxyl, lower alkoxycarbonyl, optionally substituted phenyl, substituted or unsubstituted amino or pyridyl, $R^2$ is substituted or unsubstituted amino, lower alkyl or amino acid residue, $R^3$ is carboxyl, lower alkoxycarbonyl, lower alkenyloxycarbonyl or amino acid residue, and n is 0–4, or a pharmacologically acceptable salt thereof.

26 Claims, No Drawings

LACTACYSTIN DERIVATIVES

This application is a continuation of application Ser. No. 08/579,340, filed Dec. 27, 1995, now abandoned.

FIELD OF THE INVENTION

This invention relates to lactacystin derivatives, which are derived from lactacystin produced by a microorganism strain Streptomyces sp. OM-6519 belonging to the genus Streptomyces which induces the outgrowth of neurites. These derivatives induce the outgrowth of neurites with low cytotoxicity and highly selective toxicity and are useful for pharmaceuticals.

BACKGROUND OF THE INVENTION

It is known that lactacystin of the formula

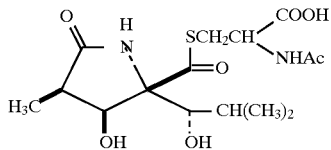

having neuritogenesis activity, is produced by culturing a physiologically active substance-producing microorganism sp. OM-6519 belonging to the genus Streptomyces, and isolating the thus-produced compound hereinabove (J. Antibiotics, 19:44, 113–116 and Japan, Pat. Unexam. Publ., No. 3-98594). However, this compound is highly cytotoxic and shows no selective toxicity.

OBJECT OF THE INVENTION

Therefore, it is an object of the present invention to provide lactacystin derivatives with a superior activity of inducing neuritogenesis and a low cytotoxicity as well as highly selective cytotoxicity.

SUMMARY OF THE INVENTION

It has now been found that lactacystin derivatives of the formula (1) hereinbelow show superior inducing activity of neuritogenesis and highly selective toxicity, compared to the known lactacystin.

Thus, the present invention comprises a lactacystin derivative of the formula

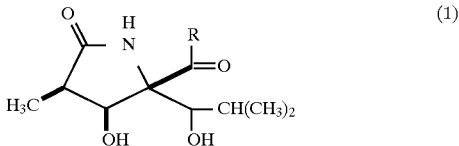

wherein R is lower alkoxy, —S—$(CH_2)_n R^1$ or —S—$(CH_2)$n—$CH(R^2)$-$(R^3)$, in which $R^1$ is branched or straight-chain lower alkyl, hydroxy, carboxyl, lower alkoxycarbonyl, optionally substituted phenyl, substituted or unsubstituted amino or pyridyl. $R^2$ is substituted or unsubstituted amino, lower alkyl or amino acid residue. $R^3$ is carboxyl, lower alkoxycarbonyl, lower alkenyloxycarbonyl or amino acid residue, and n is 0–4, or a pharmacologically acceptable salt thereof. Of course, lactacystin per se is excluded.

DETAILED DESCRIPTION OF THE INVENTION

In the definitions in the formula (1), lower alkoxy means an alkoxy group. Examples of alkoxy are methoxy, ethoxy, propoxy, isopropoxy, butoxy, isobutoxy and t-butoxy. Methoxy and ethoxy are preferred.

Lower alkoxycarbonyl means $C_{1-4}$ alkoxycarbonyl which has optionally a branched chain. Examples of alkoxycarbonyl are methoxycarbonyl, ethoxycarbonyl, propoxycarbonyl, isopropoxycarbonyl, butoxycarbonyl, isobutoxycarbonyl and t-butoxycarbonyl. Methoxycarbonyl and ethoxycarbonyl are preferred.

Optionally substituted phenyl means phenyl or substituted phenyl. Examples of substituents are hydroxy, amino, sulfonyl, nitro, carboxyl and alkyl. Hydroxy is preferred.

Substituted or unsubstituted amino means amino or mono- or dimethylamino.

Lower alkenyloxycarbonyl means $C_{1-4}$ alkenyloxycarbonyl which has optionally a branched chain. Examples of alkenyloxycarbonyl are vinyloxycarbonyl, allyloxycarbonyl, isopropenyloxycarbonyl, 1-propenyloxycarbonyl, 2-butenyloxycarbonyl and 1,3-butadienyloxycarbonyl. Allyloxycarbonyl is preferred.

Lower alkyl means $C_{1-4}$ alkyl which is optionally branched. Examples of alkyl are methyl, ethyl, propyl, isopropyl, butyl, isobutyl, sec-butyl, t-butyl, and the like. Methyl, ethyl, propyl and isopropyl are preferred.

The derivatives (1) of the present invention, when the molecule has carboxyl or amino in its structure, can be in the form of a pharmacologically acceptable salt thereof. Examples of pharmacologically acceptable salts, when the derivative (1) has carboxyl, are alkali metal salts such as sodium salt or potassium salt, and alkaline earth metal salts such as magnesium salt or calcium salt.

Pharmacologically acceptable salts with known amines or basic amino acids can also be prepared. Examples of the pharmacologically acceptable salts when the derivative (1) has amino are acid addition salts of inorganic acids such as hydrochloride, hydrobromide, sulfate or phosphate, and acid addition salts of organic acids such as acetate, malate, succinate, tartrate, citrate, oxalate, maleinate, glycolate, methanesulfonate, toluenesulfonate, aspartate or glutamate.

Lactacystin derivatives (1) can be produced, for example, by the following processes.

(a) A derivative (1) wherein R is lower alkoxy, i.e. the formula (1a)

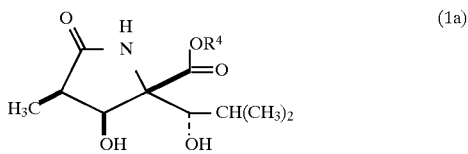

in which $R^4$ is lower alkyl, [hereinafter designated as derivative (1a)].

The derivative (1a) can be produced by reacting lactacystin with an alkoxide such as sodium alkoxide in a lower alcohol such as methanol. Examples of sodium alkoxide are sodium methoxide, sodium ethoxide, sodium propoxide, sodium isopropoxide, sodium butoxide, sodium isobutoxide and sodium t-butoxide.

The above reaction proceeds at room temperature. The reaction can be traced by TLC and HPLC, and is terminated upon maximum production of the derivative (1a).

Isolation of the derivative (1a) can be performed by neutralization of the reaction mixture with aqueous ammonium chloride, removal of solvent by evaporation and treatment of the residue by column chromatography.

(b) A derivative (1) wherein R is —S—$(CH_2)_n R^1$ or —S—$(CH_2)$nCH $(R^2)$-$(R^3)$ (n=0–4), i.e. the derivative (1b).

A derivative (1b) can be produced by reacting β-lactam (2) of the formula

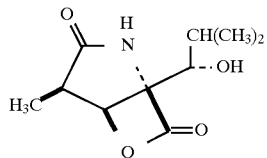

with a mercapto compound of the formula

HS—(CH$_2$)nR$^1$ or

HS—(CH$_2$)$_n$CH (R$^2$)-(R$^3$)

wherein R$^1$, R$^2$ and R$^3$ have the same meanings as hereinbefore, and n is an integer of 0–4, in the presence of a tertiary organic amine in an inert organic solvent, provided that in the formula HS—(CH$_2$)$_n$CH (R$^2$)-(R$^3$), the combination is excluded wherein n is 1, R$^2$ is NHAc, Ac is acetyl and R$^3$ is carbonyl.

Examples of inert organic solvents used in the above reaction are dichloromethane, chloroform and tetrahydrofuran. Examples of tertiary organic amines used in the above reaction are known tertiary organic amines. Trimethylamine and triethylamine are preferred.

Preferred examples of mercapto compounds are 3-mercaptopropionic acid, 3-mercaptopropionic acid methyl ester, 3-mercaptopropionic acid ethyl ester, cysteamine, cysteamine hydrochloride, N-acetyl cysteamine, N-acetyl cysteamine methyl ester, N-acetyl cysteamine ethyl ester, N-acetyl cysteamine allyl ester, ethane thiol, propane thiol, isopropane thiol, butane thiol, 1-methyl-1-propane thiol, 1-pentane thiol, thiophenol, 2-mercapto ethanol, 3-mercapto-1-propanol, 4-hydroxythiophenol, N-methylcysteine, N-dimethylcysteine, mercapto acetic acid, methylthioglycolate, methyl-3-mercapto-propionate, 2-mercapto pyridine, 4-mercapto pyridine, homocysteine, N-(2-mercaptopropionyl) glycine and glutathione.

The above reaction proceeds preferably under an inert gas such as argon or nitrogen. The reaction proceeds at room temperature. The reaction can be traced by TLC and HPLC, and is terminated upon maximum production of the derivative (1b).

Isolation of the derivative (1b) can be performed by removing solvent from the reaction mixture and treating the residue by column chromatography.

The thus-obtained derivative (1) can be further purified by conventional means for the isolation and purification of organic compounds, for example a combination of extraction, crystallization and chromatography.

Pharmacologically acceptable salts of the derivative (1) can be prepared by conventional methods for preparation of the salt.

Examples of the derivatives of the present invention are as follows.

τ-lactam methyl ester (2)
   R: OCH$_3$
desacetylamino lactacystin (3)
   R: —S—CH$_2$CH$_2$COOH
desacetylamino lactacystin ethyl ester (4)
   R: —S—CH$_2$CH$_2$COOC$_2$H$_5$
desacetyl descarboxy lactacystin (5)
   R: —S—CH$_2$CH$_2$NH$_2$
lactacystin methyl ester (6)
   R —S—CH$_2$CH(NHAc)COOCH$_3$
   (wherein Ac is acetyl)

lactacystin allyl ester (7)
   R: —S—CH$_2$CH(NHAc)COOCH$_2$CH=CH$_2$
   (wherein Ac is acetyl)
3-hydroxy-2-(1-hydroxy-2-methylpropyl)-4-methyl-5-oxo-2-pyrrolidine-ethanethiocarboxylate (8)
   R: —S—CH$_2$CH$_3$
3-hydroxy-2-(1-hydroxy-2-methylpropyl)-4-methyl-5-oxo-2-pyrrolidine-propanethiocarboxylate (9)
   R: —S—(CH$_2$)$_2$CH$_3$
3-hydroxy-2-(1-hydroxy-2-methylpropyl)-4-methyl-5-oxo-2-pyrrolidine-iso-propanethiocarboxylate (10)
   R: —S—CH(CH$_3$)$_2$
3-hydroxy-2-(1-hydroxy-2-methylpropyl)-4-methyl-5-oxo-2-pyrrolidine-butanethiocarboxylate (11)
   R: —S—(CH$_2$)$_3$CH$_3$
3-hydroxy-2-(1-hydroxy-2-methylpropyl)-4-methyl-5-oxo-2-pyrrolidine-1-methyl-1-propanethiocarboxylate (12)
   R: —S—CH$_2$CH(CH$_3$)$_2$
3-hydroxy-2-(1-hydroxy-2-methylpropyl)-4-methyl-5-oxo-2-pyrrolidine-1-pentanethiocarboxylate (13)
   R: —S—(CH$_2$)$_4$CH$_3$
3-hydroxy-2-(1-hydroxy-2-methylpropyl)-4-methyl-5-oxo-2-pyrrolidine-phenylthiocarboxylate (14)
   R:

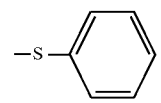

3-hydroxy-2-(1-hydroxy-2-methylpropyl)-4-methyl-5-oxo-2-pyrrolidine-2-hydroxyethanethiocarboxylate (15)
   R: —S—CH$_2$CH$_2$OH
3-hydroxy-2-(1-hydroxy-2-methylpropyl)-4-methyl-5-oxo-2-pyrrolidine-3-hydroxypropanethiocarboxylate (16)
   R: —S—CH$_2$CH$_2$CH$_2$OH
3-hydroxy-2-(1-hydroxy-2-methylpropyl)-4-methyl-5-oxo-2-pyrrolidine-4-hydroxyphenylthiocarboxylate (17)
   R:

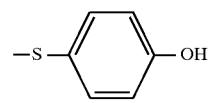

3-hydroxy-2-(1-hydroxy-2-methylpropyl)-4-methyl-5-oxo-2-pyrrolidine-2-N-methyl-ethanethiocarboxylate (18)
   R: —S—CH$_2$CH$_2$NHCH$_3$
3-hydroxy-2-(1-hydroxy-2-methylpropyl)-4-methyl-5-oxo-2-pyrrolidine-2-N-dimethyl-ethanethiocarboxylate (19)
   R: —S—CH$_2$CH$_2$N(CH$_3$)$_2$
3-hydroxy-2-(1-hydroxy-2-methylpropyl)-4-methyl-5-oxo-2-pyrrolidine-1-carboxymethylthiocarboxylate (20)
   R: —S—CH$_2$COOH
3-hydroxy-2-(1-hydroxy-2-methylpropyl)-4-methyl-5-oxo-2-pyrrolidine-methoxycarbonylmethylthiocarboxylate (21)
   R: —S—CH$_2$COOCH$_3$ 3-hydroxy-2-(1-hydroxy-2-methylpropyl)-4-methyl-5-oxo-2-pyrrolidine-methoxycarbonylethylthiocarboxylate (22)
R: —S—CH₂CH₂COOCH₃

3-hydroxy-2-(1-hydroxy-2-methylpropyl)-4-methyl-5-oxo-2-pyrrolidine-2-pyridylthiocarboxylate (23)
R:

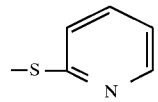

3-hydroxy-2-(1-hydroxy-2-methylpropyl)-4-methyl-5-oxo-2-pyrrolidine-4-pyridylthiocarboxylate (24)
R:

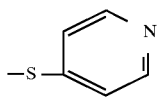

Homocysteine-3-hydroxy-2-(1-hydroxy-2-methylpropyl)-4-methyl-5-oxo-2-pyrrolidine-carboxylate (25)
R: —S—CH₂CH₂CH(NH₂)COOH 2—S-propionylglycine-3-hydroxy-2-(1-hydroxy-2-methyl-propyl)-4-methyl-5-oxo-2-pyrrolidinecarboxylate (26)
R:

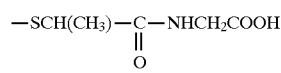

Glutathione-3-hydroxy-2-(1-hydroxy-2-methylpropyl)-4-methyl-5-oxo-2-pyrrolidinethiocarboxylate (27)
R:

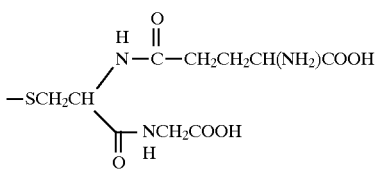

Test Results

The pharmacological activity of the derivative (1) and its pharmacologically acceptable salts are set forth hereinbelow.

1. Activity of neuritogenesis and cytotoxic action:
(1) Test method:
Morphological changes of Neuro 2A cells are observed according to the method of Baglioni et al. [J. Biol. Chem., 266: 18620 (1991)].

Neuro 2A cells were plated at a density of 1×10⁴ cells/cm² in a 24-hole plate, and cultured in MEM-H with 10% FBS. On the next day, lactacystin or lactacystin derivatives were added at the concentration of 0.05–100 μM, and morphological changes of the cells with time were observed by phase contrast microscopy.

Minimum effective dose of the substances was defined as a concentration in which approximately 20% of whole cells showed induction of bipolar outgrowth of neurites.

Cytotoxicity of the compounds is defined as when no attached Neuro 2A cells were observed in more than ⅔ of the whole cells.

(2) Results:
The results of the tests are shown in Table 1.

2. No specific test method for selective toxicity of the compounds is known, therefore the selective toxicity is defined as the ratio of cytotoxicity/minimum effective dose.
The results are shown in Table 1.

TABLE 1

| Compound (Example No.) | Minimum effective dose (μM) (A) | Cytotoxicity (μM) (B) | Selective toxicity (B/A) |
|---|---|---|---|
| 1 | 1.56 | 12.5 | 8 |
| 2 | 0.20 | 1.56 | 8 |
| 3 | 0.20 | 3.12 | 16 |
| 4 | 3.12 | 25 | 8 |
| 5 | 0.78 | 6.25 | 8 |
| 6 | 0.20 | 6.25 | 31 |
| 7 | 0.20 | 1.56 | 8 |
| 8 | 0.20 | 3.12 | 16 |
| 9 | 0.40 | 12.5 | 31 |
| 10 | 0.40 | 12.5 | 31 |
| 11 | 0.40 | 12.5 | 31 |
| 12 | 0.80 | 12.5 | 16 |
| 13 | 0.80 | 12.5 | 16 |
| 14 | 3.12 | 25 | 8 |
| 15 | 0.40 | 12.5 | 31 |
| 16 | 0.40 | 12.5 | 31 |
| 17 | 0.80 | 6.25 | 8 |
| 18 | 0.20 | 6.25 | 31 |
| 19 | 0.40 | 12.5 | 31 |
| 20 | 0.80 | 12.5 | 16 |
| 21 | 0.20 | 1.56 | 8 |
| 22 | 0.80 | 12.5 | 16 |
| 23 | 0.80 | 12.5 | 16 |
| 24 | 1.56 | 25 | 16 |
| 25 | 1.56 | 12.5 | 8 |
| 26 | 0.80 | 25 | 31 |

As shown in Table 1, the derivative (1) or a pharmacologically acceptable salt thereof of the present invention is superior for inducing the activity of outgrowth of neurites, as compared to the known lactacystin, and has higher selective toxicity as to the cells. Therefore, novel lactacystin derivatives are provided which are more effective than the known lactacystin.

The compounds of the present invention, as well as lactacystin, are the neurotrophic factor, and induce neuritogenesis and cause a transient increase in the intracelluar cAMP level in mouse neuroblastoma cell line Neuro 2A. Therefore lactacystin derivative of the present invention is expected to be useful also in the treatment of dementia. Accordingly the compounds of the present invention are expected to be applied as a neurotrophic drug.

Dosage is usually approximately 200 mg/person per day i.v. When the compound of the present invention is administered 100 mg/kg i.p. in mice, no death is observed.

The following examples and referential examples illustrate preferred embodiments of the present invention but are not to be construed as limiting.

REFERENTIAL EXAMPLE 1

Lactacystin (45.5 mg) dissolved in ethanol (0.31 ml) and 0.1N sodium hydroxide (0.93 ml) was stirred at room temperature for 30 minutes. The reaction mixture was neutralized with the addition of 2N HCl and dried in vacuo. The residue was purified by preparative TLC (developer, THF:H₂O=10:1) to obtain τ-lactam 26.2 mg (yield:94.0%).

¹H-NMR (270 MHz, CD₃OD) δ 0.85 (d, J=6.6 Hz, 3H, (CH₃)₂CH), 0.86 (d, J=6.6 Hz, 3H, (CH₃) ₂CH), 0.98 (d, J=7.6 Hz, HOCHCHCH₃) 1.69 (m, 1H, (CH₃)₂CH), 2.86 (m, 1H, HOCHCHCH₃), 3.83 (d, J=5.3 Hz, 1H, HOCH), 4.30 (d, J=5.9 Hz, 1H, HOCHCHCH₃)

LRMS (FAB, Glycerol matrix) m/z232 [(M+H)$^+$; calcd for $C_{10}H_{18}NO_5$:232]

EXAMPLE 1

Sodium methoxide (1.9 mg) was added to lactacystin (8.5 mg) dissolved in methanol (0.5 ml) and the mixture was stirred at room temperature for 1 hour. The reaction mixture was neutralized with saturated aqueous ammonium chloride, dried in vacuo and purified with preparative TLC (developer, chloroform:methanol=10:1) to obtain τ-lactam methyl ester (2) 4.8 mg (yield:87%).

$^1$H-NMR (270 MHz, CD$_3$OD) δ 0.84 (d, J=6.6 Hz, 3H, (CH$_3$)$_2$CH), 0.88 (d, J=6.6 Hz, 3H, (CH$_3$)$_2$CH), 1.06 (d, J=7.3 Hz, 3H, HOCHCHCH$_3$), 1.65 (m, 1H, (CH$_3$)$_2$CH), 2.94 (m, 1H, HOCHCHCH$_3$), 3.72 (s, 3H, OCH$_3$), 3.90 (d, J=7.3 Hz, 1H, HOCH), 4.43 (d, J=5.9 Hz, 1H, HOCHCHCH$_3$)

LRMS (FAB, Glycerol matrix) m/z246 [(M+H)$^+$; calcd for $C_{11}H_{20}NO_5$:246]

REFERENTIAL EXAMPLE 2

τ-lactam (43.3 mg, 0.187 mmol) was dissolved in dichloromethane (0.7 ml) under an argon atmosphere. BOPCl (1.5 eq., 0.305 mmol, 77.6 mg) and triethylamine (3 eq., 0.609 mmol, 85 μl) were added thereto. The reaction mixture was stirred at room temperature for 70 minutes, cooled to 0° C., and water was added thereto to stop the reaction. The reaction mixture was transferred into a separating funnel, extracted with chloroform and dried by adding Na$_2$SO$_4$. The extract was concentrated in vacuo and purified using silica gel column chromatography (extracting solvent, CHCl$_3$:MeOH=50:1) to obtain β-lactone 27.2 mg (yield:68.0%).

$^1$H-NMR (270 MHz, CD$_3$Cl$_3$) δ 0.84 (d, J=6.8 Hz, 3H, (CH$_3$)$_2$CH), 0.99 (d, J=6.8 Hz, 3H, (CH$_3$)$_2$CH), 1.27 (d, J=7.6 Hz, 3H, CH$_3$CHCHOH), 1.82 (m, 1H, (CH$_3$)$_2$CH), 2.69 (m, 1H, CH$_3$CHCHOH), 3.91 (d, J=6.9 Hz, 1H, HOCHCH), 5.15 (d, J=6 3 Hz, 1H, CH$_3$CHCHOH), 6.25 (s, 1H, NH)

$^{13}$C-NMR (67.5 MHz, CDCl$_3$ δ 8.1, 16.3, 20.0, 29.6, 38.1, 64.0, 71.8, 76.0, 171.1, 176.8

LRMS (FAB, NBA matrix) m/z214 [(M+H)$^+$; Calcd for $C_{10}H_{16}NO_4$:214]

EXAMPLE 2

β-lactone (9.3 mg, 0.044 mmol) obtained by the method of Referential Example 2 was dissolved in dichloromethane (0.8 ml) under an argon atmosphere. Triethylamine (6 eq., 0.264 mmol, 36.8 μl) and mercapto propionic acid (3 eq., 0.066 mmol, 12 μl) were added thereto. The reaction mixture was stirred at 40° C. for 2 days, concentrated in vacuo and purified using preparative TLC (developer, CHCl$_3$:MeOH= 1:1) to obtain des-N-acetylaminolactacystin 6.5 mg (yield:47%).

$^1$H-NMR (270 MHz, CD$_3$OD) δ 0.79 (d, J=6.6 Hz, 3H, (CH$_3$)$_2$CH), 0.87 (d, J=6.6 Hz, 3H, (CH$_3$)$_2$CH), 0.98 (d, J=7.6 Hz, 3H, CH$_3$CHCHOH), 1.58 (m, 1H, (CH$_3$)$_2$CH), 2.47 (m, 2H, SCH$_2$CH$_2$COOH), 2.83 (m, 1H, CH$_3$CHCHOH), 2.99 (m, 2H, SCH$_2$CH$_2$COOH), 3.86 (d, J=6.9 Hz, 1H HOCHCH), 4.43 (d, J=6.6 Hz, 1H, CH$_3$CHCHOH)

LRMS (FAB, NBA matrix) m/z320 [(M+H)$^+$; calcd for $C_{13}H_{22}NO_6S$:320]

EXAMPLE 3

β-lactone (13 mg, 0.06 mmol) obtained by the method of Referential Example 2 was dissolved in dichloromethane (866 μl) under an argon atmosphere. Triethylamine (3 eq., 0.18 mmol, 25.1 μl) and 3-mercapto propionic acid ethyl ester (1.5 eq., 0.09 mmol, 12.1 μl) were added thereto. The reaction mixture was stirred at room temperature for 70 minutes, concentrated in vacuo and purified using preparative TLC (developer, CHCl$_3$:MeOH=10:1, Rf=0.19) to obtain des-N-acetylaminolactacystin ethyl ester 18.8 mg (yield:89%).

$^1$H-NMR (400MH$_2$, CDCl$_3$) δ 0.96 (d, J=7.0 Hz, 6H, (CH$_3$), 1.18 (d, J=7.5 Hz, 3H, CH$_3$CHCHOH), 1.26 (t, J=7.0 Hz, 3H, OCH$_2$CH$_3$) 1.58 (b s, 2H, OH×2), 1.78 (m, 1H, (CH$_3$)$_2$CH), 2.62 (t, J=7.01 Hz, 2H, S(CH$_2$)$_2$), 2.95 (m, 1H, HOCHCHCH$_3$), 3.19 (t, J=7.0 Hz, 2H, S(CH$_2$)$_2$)$_2$), 4.05 (d, J=5.0 Hz, 1H, HOCHCH), 4.15 (q, J=7.0, 2H, OCH$_2$CH$_3$), 4.66 (d, J=7.0 Hz, 1H, HOCHCHCH$_3$), 6.07 (S, 1H, NH)

$^{13}$C-NMR (100 MHz, CDCl$_3$) δ 8.8, 14.2, 17.2 21.0, 24.4, 30.8, 33.8, 40.5, 61.0, 76.1, 78.7, 79.1, 128.8, 171.4, 179.7, 201.4 HRMS (FAB, NBA matrix) m/z347.1405 [(M+H)$^+$; calcd for $C_{15}H_{25}NO_6S$:347.1402]

EXAMPLE 4

β-lactone (8.7 mg, 0.038 mmol) obtained by the method of Referential Example 2 was dissolved in tetrahydrofuran (0.8 ml) under an argon atmosphere. Triethylamine (3 eq., 0.114 mmol, 16 μl) and cysteamine (1.5 eq., 0.057 mmol, 6.5 mg) were added thereto. The reaction mixture was stirred at room temperature for 2 hours, concentrated in vacuo and purified using preparative TLC (developer, CHCl$_3$:MeOH= 3:1) to obtain des-N-acetyldescarboxylactacystin 5.7 mg (yield:48.0%).

$^1$H-NMR (270 MHz, CD$_3$OD) δ 0.90 (d, J=7.6 Hz, 3H, (CH$_3$)$_2$CH), 0.97 (d, J=7.6 Hz, 3H, (CH$_3$)$_2$CH), 1.10 (d, J=7.3 Hz, 3H, H$_3$CCHCHOH), 1.67 (m, 1H, (CH$_3$)$_2$CH), 2.85 (t, J=9.8 Hz, 2H, S(CH$_2$)$_2$), 2.88 (m, 1H, CH$_3$CHCHOH), 3.57 (t, J=9.8 Hz, 2H, S(CH$_2$)$_2$), 4.04 (d, J=6.3 Hz, 1H, HOCHCH), 4.48 (d, J=6.3 Hz, 1H, CH$_3$CHCHOH)

HRMS (FAB, NBA matrix) m/z291 [(M+H)$^+$; calcd for $C_{12}H_{23}N_2O_4S$:291]

EXAMPLE 5

β-lactone (5.0 mg, 0.023 mmol) obtained by the method of Referential Example 2 was dissolved in dichloromethane (433 μl) under an argon atmosphere. Triethylamine (3 eq., 0.07 mmol, 10 μl) and N-acetylcysteine methyl ester (1.5 eq., 0.36 mmol, 6.8 mg) were added thereto. The reaction mixture was stirred at room temperature for 20 minutes, concentrated in vacuo and purified using preparative TLC (developer, CHCl$_3$:MeOH=8:1) to obtain lactacystin methyl ester 8.1 mg (yield:89%).

$^1$H-NMR (270 MHz, CD$_3$OD) δ 0.76 (d, J=6.6 Hz, 3H, (CH$_3$)$_2$CH), 0.88 (d, J=6.6 Hz, 3H, (CH$_3$)$_2$CH), 1.02 (d, J=7.6 Hz, 3H, CH$_3$CH), 1.56 (m, 1H, (CH$_2$)$_2$CH), 1.86(S, 3H, COCH$_3$), 2.76(m, 1H, CH$_3$CH), 3.12 (d d, J=13.9, 6.9 Hz, 1H, SCH$_2$), 3.38 (d d, J=13.9, 5.0 Hz, 1H, SCH$_2$), 3.63 (S, 3H, COOCH$_3$), 3.83 (d, J=6.6 Hz, HOCHCHCH$_3$), 4.50 (d, J=7.9 Hz, 1H, CHCHOH), 4.55 (m, 1H, SCH$_2$CH), 8.03 (d, J=7.6 Hz, 1H, NH)

LRMS (FAB, NBA matrix) m/z391 [(M+H)$^+$; calcd for $C_{16}H_{27}N_2O_7S$:391]

EXAMPLE 6

β-lactone (9.9 mg, 0.047 mmol) obtained by the method of Referential Example 2 was dissolved in dichloromethane (866 μl) under an argon atmosphere. Triethylamine (3 eq., 0.14 mmol, 20 μl) and N-acetylcysteine allyl ester (1.5 eq., 0.07 mmol, 14.3 mg) were added thereto. The reaction mixture was stirred at room temperature for 30 minutes, concentrated in vacuo and purified using preparative TLC (developer, $CHCl_3$:MeOH=8:1, Rf=0.52) to obtain lactacystin allyl ester 15.6 mg (yield:80.8%).

m. p.:182–184 (decomp.) $[\alpha]_D^{23}$=+33.8° (C=0.5, $CHCl_3$)

IR ($CCl_4$) 3700 (W), 3450 (W), 3025 (S), 2975 (m), 2925 (m), 2400 (m), 1710 (S), 1680 (S), 1500 (m), 1480 (m), 1420 (m), 1380 (m), 1330 (W), 1210 (S), 1040 (m), 880 (W), 850 (W), 690 (S) $cm^{-1}$ $^1$H-NMR (270 MHz, $CDCl_3$) δ 0.85 (d, J=6.6 Hz, 3H, $(CH_3)_2CH$), 0.92 (d, J=6.6 Hz, 3H, $(CH_3)_2CH$), 1.12 (d, J=7.5 Hz, 3H, $HOCHCHCH_3$), 1.69 (m, 1H, $(CH_3)_2CH$), 1.94 (S, 3H, $NCOCH_3$), 2.86 (m, 1H, $HOCHCHCH_3$), 3.17 (d d, J=14.1, 6.3 Hz, 1H, $SCH_2$), 3.55 (d d, J=14.1, 4.3 Hz, 1H, $SCH_2$), 4.00 (d, J=5.9 Hz, 1H, CHCHOH), 4.51 (d, J=5.6 Hz, 1H, $HOCHCHCH_3$), 4.57 (m, 2H, $CH_2=CHCH_2O$), 4.81 (m, 1H, $SCH_2CH$), 5.25 (d d, J=15.0, 8.4 Hz, 2H, $CH_2=CH$), 5.86 (m, 1H, $OCH_2CH=CH_2$), 6.20 (d, J=7.6 Hz, 1H, NH), 6.28 (S, 1H, NH)

$^{13}$C-NMR (67.5 MHz, $CDCl_3$) δ 7.8, 16.7 20.9, 29.7, 30.2, 36.5, 40.3, 51.3, 66.6, 75.4, 78.1, 79.1, 119.4, 131.0, 170.0, 170.2, 179.6, 203.1

HRMS (FAB NBA matrix) m/z439.1519 [(M+H)$^+$; calcd for $C_{18}H_{28}N_2O_7SNa$:439.1515]

EXAMPLE 7

β-lactone (10 mg, 0.047 mmol) obtained by the method of Referential Example 2 was dissolved in dichloromethane (1.0 ml) under an argon atmosphere. Triethylamine (6 eq., 0.0282 mmol, 39.3 μl) and ethanethiol (3 eq., 0.141 mmol, 10.4 μl) were added thereto. The reaction mixture was stirred at 40° C. for 1 hour, concentrated in vacuo and purified using preparative TLC (developer, $CHCl_3$:MeOH=10:1) to obtain 3-hydroxy-2-(1-hydroxy-2-methylpropyl)-4-methyl-5-oxo-2-pyrrolidine-ethanethiocarboxylate 10.3 mg (yield:80%).

$^1$H-NMR (270 MHz, $CDCl_3$) δ 0.79 (d, J=6.6H, 3H), 0.87 (d, J=6.6 Hz, 3H), 0.98 (d, J=7.6 Hz, 3H), 1.05 (t, J=8.5 Hz, 3H) 1.58 (m, 1H), 2.25 (q, J=8.5 Hz, 2H), 2.83 (m, 1H), 3.86 (d, J=6.9 Hz, 1H), 4.43 (d, J=6.6 Hz, 1H)

LRMS (FAB, NBA matrix) m/z276 [(M+H)$^+$; calcd for $C_{12}H_{22}NO_4S$:276]

EXAMPLE 8

β-lactone (10 mg, 0.047 mmol) obtained by the method of Referential Example 2 was dissolved in dichloromethane (1.0 ml) under an argon atmosphere. Triethylamine (6 eq., 0.0282 mmol, 39.3 μl) and propanethiol (3 eq., 0.14 mmol, 14.5 μl) were added thereto. The reaction mixture was stirred at 40° C. for 1 hour, concentrated in vacuo and purified using preparative TLC (developer, $CHCl_3$:MeOH=10:1) to obtain 3-hydroxy-2-(1-hydroxy-2-methylpropyl)-4-methyl-5-oxo-2-pyrrolidine-propanethiocarboxylate 10.6 mg (yield:78%).

$^1$H-NMR (270 MHz, $CDCl_3$), δ 0.79 (d, J=6.6H, 3H), 0.87 (d, J=6.6 Hz, 3H), 0.98 (d, J=7.6 Hz, 3H), 1.05 (t, J=8.5 Hz, 3H),1.40 (m, 2H), 1.58 (m, 1H), 2.25 (q, J=7.5 Hz, 2H), 2.83 (m, 1H), 3.86 (d, J=6.9 Hz, 1H), 4.43 (d, J=6.6 Hz, 1H)

LRMS (FAB, NBA matrix) m/z290 [(M+H)$^+$; calcd for $C_{13}H_{24}NO_4S$:290]

EXAMPLE 9

β-lactone (10 mg, 0.047 mmol), obtained by the method of Referential Example 2 was dissolved in dichloromethane (1.0 ml), under an argon atmosphere. Triethylamine (6 eq., 0.0282 mmol, 39.3 μl), and iso-propanethiol (3 eq., 0.141 mmol, 14.5 μl) were added thereto. The reaction mixture was stirred at 60° C. for 3 hours, concentrated in vacuo and purified using preparative TLC (developer, $CHCl_3$:MeOH=10:1), to obtain 3-hydroxy-2-( 1-hydroxy-2-methylpropyl)-4-methyl-5-oxo-2-pyrrolidine-iso-propanethiocarboxylate 8.8 mg (yield:65%).

$^1$H-NMR (270 MHz, $CDCl_3$) δ 0.79 (d, J=6.6H, 3H), 0.87 (d, J=6.6 Hz, 3H), 0.98 (d, J=7.6 Hz, 3H), 1.50 (d, J=8.5 Hz, 6H), 1.58 (m, 1H), 2.53 (m, 1H), 2.83 (m, 1H), 3.86 (d, J=6.9 Hz, 1H), 4.43 (d, 6.6 Hz, 1H)

LRMS (FAB, NBA matrix) m/z290 [(M+H)$^+$; calcd for $C_{13}H_{24}NO_4S$:290]

EXAMPLE 10

β-lactone (10 mg, 0.047 mmol), obtained by the method of Referential Example 2 was dissolved in dichloromethane (1.0 ml), under an argon atmosphere. Triethylamine (6 eq., 0.0282 mmol, 39.3 μl), and butanethiol (3 eq., 0.14 mmol, 15.1 μl), were added thereto. The reaction mixture was stirred at 60° C. for 5 hours, concentrated in vacuo and purified using preparative TLC (developer, $CHCl_3$:MeOH=10:1), to obtain 3-hydroxy-2-(1-hydroxy-2-methylpropyl)-4-methyl-5-oxo-2-pyrrolidine-butanethiocarboxylate 8.5 mg (yield:62%).

$^1$H-NMR (270 MHz, $CDCl_3$) δ 0.79 (d, J=6.6H, 3H), 0.87 (d, J=6.6 Hz, 3H), 0.90 (t, J=8.5 Hz, 3H), 0.98 (d, J=7.61 Hz, 3H), 1.20~1.30 (m, 4H), 1.30 (m, 2H), 1.58 (m, 1H), 2.25 (q, J=8.5 Hz, 2H), 2.83 (m, 1H), 3.86 (d, J=6.9 Hz, 1H), 4.43 (d, J=6.6 Hz, 1H)

LRMS (FAB, NBA matrix) m/z304 [(M+H)$^+$; calcd $C_{14}H_{26}NO_4S$:304]

EXAMPLE 11

β-lactone (10 mg, 0.047 mmol), obtained by the method of Referential Example 2 was dissolved in dichloromethane (1.0 ml), under an argon atmosphere. Triethylamine (6 eq., 0.0282 mmol, 39.3 μl), and 1-methyl-1-propanethiol (3 eq., 0.141 mmol, 10.4 μl), were added thereto. The reaction mixture was stirred at 60° C. for 15 hours, concentrated in vacuo and purified using preparative TLC (developer, $CHCl_3$:MeOH=20:1), to obtain 3-hydroxy-2-(1-hydroxy-2-methylpropyl)-4-methyl-5-oxo-2-pyrrolidine-1-methyl-1-propanethiocarboxylate 7.8 mg (yield:55%).

$^1$H-NMR (270 MHz, $CDCl_3$) δ 0.79 (d, J=6.6H, 3H), 0.87 (d, J=6.6 Hz, 3H), 0.98 (d, J=7.6 Hz, 3H), 1.05 (d, J=8.5 Hz, 6H), 1.40 (m, 1H), 1.58 (m, 1H), 2.25 (q, J=8.5 Hz, 2H), 2.83 (m, 1H), 3.86 (d, J=6.9 Hz, 1H), 4.43 (d, J=6.6 Hz, 1H)

LRMS (FAB, NBA matrix) m/z304 [(M+H)$^+$; calcd for $C_{14}H_{26}NO_4S$:304]

EXAMPLE 12

β-lactone (10 mg, 0.047 mmol), obtained by the method of Referential Example 2 was dissolved in dichloromethane (1.0 ml), under an argon atmosphere. Triethylamine (6 eq., 0.0282 mmol, 39.3 μl), and 1-pentanethiol (6 eq., 0.282 mmol, 35.0 μl) were added thereto. The reaction mixture was stirred at 40° C. for 6 hours, concentrated in vacuo and purified using preparative TLC (developer, $CHCl_3$:MeOH=20:1), to obtain 3-hydroxy-2-( 1-hydroxy-2-methylpropyl)-4-methyl-5-oxo-2-pyrrolidine-1-pentanethiocarboxylate 10.4 mg (yield:70%).

$^1$H-NMR (270 MHz, $CDCl_3$) δ 0.79 (d, J=6.6H, 3H), 0.80 (q, J=8.5 Hz, 3H), 0.87 (d, J=6.6 Hz, 3H), 0.98 (d, J=7.6 Hz,

3H), 1.20~1.40 (m, 6H), 1.58 (m, 1H), 2.25 (q, J=8.5 Hz, 2H), 2.83 (m, 1H), 3.86 (d, J=6.9 Hz, 1H), 4.43 (d, J=6.6 Hz, 1H)

LRMS (FAB, NBA matrix) m/z318 [(M+H)$^+$; calcd for $C_{15}H_{28}NO_4S$:318]

EXAMPLE 13

β-lactone (10 mg, 0.047 mmol), obtained by the method of Referential Example 2 was dissolved in dichloromethane (1.0 ml), under an argon atmosphere. Triethylamine (6 eq., 0.0282 mmol, 39.3 μl), and thiophenol (6 eq., 0.282 mmol, 29.2 μl), were added thereto. The reaction mixture was stirred at 40° C. for 1 hour, concentrated in vacuo and purified using preparative TLC (developer, CHCl$_3$:MeOH=20:1), to obtain 3-hydroxy-2-(1-hydroxy-2-methylpropyl)-4-methyl-5-oxo-2-pyrrolidine-phenythiocarboxylate 12.1 mg (yield:80%).

$^1$H-NMR (270 MHz, CDCl$_3$) δ 0.79 (d, J=6.6H, 3H), 0.87 (d, J=6.6 Hz, 3H), 0.98 (d, J=7.6 Hz, 3H), 1.58 (m, 1H), 2.83 (m, 1H), 3.86 (d, J=6.9 Hz, 1H), 4.43 (d, J=6.6 Hz, 1H), 7.10~7.50 (m, 5H)

LRMS (FAB, NBA matrix) m/z324 [(M+H)$^+$; calcd for $C_{16}H_{22}NO_4S$:324]

EXAMPLE 14

β-lactone (10 mg, 0.047 mmol), obtained by the method of Referential Example 2 was dissolved in dichloromethane (1.0 ml), under an argon atmosphere. Triethylamine (6 eq., 0.0282 mmol, 39.3 μl), and 2-mercapto ethanol (3 eq., 0.141 mmol, 10.0 μl), were added thereto. The reaction mixture was stirred at 40° C. for 1 hour, concentrated in vacuo and purified using preparative TLC (developer, CHCl$_3$:MeOH=10:1), to obtain 3-hydroxy-2-(1-hydroxy-2-methylpropyl)-4-methyl-5-oxo-2-pyrrolidine-2-hydroxyethanethiocarboxylate 9.3 mg (yield:68%).

$^1$H-NMR (270 MHz, CDCl$_3$) δ 0.79 (d, J=6.6H, 3H), 0.87 (d, J=6.6 Hz, 3H), 0.98 (d, J=7.6 Hz, 3H), 1.58 (m, 1H), 2.45 (t, J=8.5 Hz, 2H), 2.83 (m, 1H), 3.86 (d, J=6.9 Hz, 1H), 3.95 (m, 2H), 4.43 (d, J=6.6 Hz, 1H)

LRMS (FAB, NBA matrix) m/z292 [(M+H)$^+$; calcd for $C_{12}H_{22}NO_5S$:292]

EXAMPLE 15

β-lactone (10 mg, 0.047 mmol), obtained by the method of Referential Example 2 was dissolved in dichloromethane (1.0 ml), under an argon atmosphere. Triethylamine (6 eq., 0.0282 mmol, 39.3 μl), and 3-mercapto-1-propanol (3 eq., 0.141 mmol, 12.3 μl), were added thereto. The reaction mixture was stirred at 40° C. for 7 hours, concentrated in vacuo and purified using preparative TLC (developer, CHCl$_3$:MeOH=10:1), to obtain 3-hydroxy-2-( 1-hydroxy-2-methylpropyl)-4-methyl-5-oxo-2-pyrrolidine-3-hydroxypropanethiocarboxylate 10.6 mg (yield:78%).

$^1$H-NMR (270 MHz, CDCl$_3$) δ 0.79 (d, J=6.6H, 3H), 0.87 (d, J=6.6 Hz, 3H), 0.98 (d, J=7.6 Hz, 3H), 1.05 (t, J=8.5 Hz, 3H), 1.40 (m, 2H), 1.50 (m, 2H), 1.58 (m, 1H), 2.25 (t, J=7.5 Hz, 2H), 2.83 (m, 1H), 3.86 (d, J=6.9 Hz, 1H), 3.95 (m, 2H), 4.43 (d, J=6.6 Hz, 1H)

LRMS (FAB, NBA matrix) m/z306 [(M+H)$^+$; calcd for $C_{13}H_{24}NO_5S$:306]

EXAMPLE 16

β-lactone (10 mg, 0.047 mmol), obtained by the method of Referential Example 2 was dissolved in dichloromethane (1.0 ml), under an argon atmosphere. Triethylamine (6 eq., 0.0282 mmol, 39.3 μl), and 4-hydroxythiophenol (6 eq., 0.282 mmol, 35.5 mg), were added thereto. The reaction mixture was stirred at 40° C. for 3 hours, concentrated in vacuo and purified using preparative TLC (developer, CHCl$_3$:MeOH=20:1), to obtain 3-hydroxy-2-(1-hydroxy-2-methylpropyl)-4-methyl-5-oxo-2-pyrrolidine-4-hydroxyphenylthiocarboxylate 12.1 gmg (yield:80%).

$^1$H-NMR (270 MHz, CDCl$_3$) δ 0.79 (d, J=6.6H, 3H), 0.87 (d, J=6.6 Hz, 3H), 0.98 (d, J=7.6 Hz, 3H), 1.58 (m, 1H), 2.83 (m, 1H), 3.86 (d, J=6.9 Hz, 1H), 4.43 (d, J=6.6 Hz, 1H), 7.50~8.00 (m, 4H)

LRMS (FBA, NBA matrix) m/z340 [(M+H)$^+$; calcd for $C_{16}H_{22}NO_5S$:340]

EXAMPLE 17

β-lactone (10 mg, 0.047 mmol), obtained by the method of Referential Example 2 was dissolved in dichloromethane (1.0 ml), under an argon atmosphere. Triethylamine (6 eq., 0.0282 mmol, 39.3 μl), and N-methylcysteine (3 eq., 0.141 mmol, 12.8 mg) were added thereto. The reaction mixture was stirred at 40° C. for 5 hours, concentrated in vacuo and purified using preparative TLC (developer, CHCl$_3$:MeOH=10:1), to obtain 3-hydroxy-2-(1-hydroxy-2-methylpropyl)-4-methyl-5-oxo-2-pyrrolidine-2-N-methylethanethiocarboxylate 12.9 mg (yield:85%).

$^1$H-NMR (270 MHz, CDCl$_3$) δ 0.79 (d, J=6.6H, 3H), 0.87 (d, J=6.6 Hz, 3H), 0.98 (d, J=7.6 Hz, 3H), 2.05 (m, 2H), 2.27 (s, 3H), 2.45 (t, J=8.5 Hz, 2H), 2.83 (m, 1H), 3.86 (d, J=6.9 Hz, 1H), 4.43 (d, J=6.61 Hz, 1H)

LRMS (FAB, NBA matrix) m/z305 [(M+H)$^+$; calcd for $C_{13}H_{25}N_2O_4S$:305]

EXAMPLE 18

β-lactone (10 mg, 0.047 mmol), obtained by the method of Referential Example 2 was dissolved in dichloromethane (1.0 ml), under an argon atmosphere. Triethylamine (6 eq., 0.0282 mmol, 39.3 μl), and N-dimethylcysteine (3 eq., 0.141 mmol, 14.9 mg), were added thereto. The reaction mixture was stirred at 60° C. for 5 hours, concentrated in vacuo and purified using preparative TLC (developer, CHCl$_3$:MeOH=20:1), to obtain 3-hydroxy-2-( 1-hydroxy-2-methylpropyl)-4-methyl-5-oxo-2-pyrrolidine-2-N-dimethyl-ethanethiocarboxylate 21.0 mg (yield:70%).

$^1$H-NMR (270 MHz, CDCl$_3$) δ 0.79 (d, J=6.6H, 3H), 0.87 (d, J=6.6 Hz, 3H), 0.98 (d, J=7.6 Hz, 3H), 2.05 (m, 2H), 2.25 (s, 6H), 2.45 (t, J=8.5 Hz, 2H), 2.83 (m, 1H), 3.86 (d, J=6.9 Hz, 1H), 4.43 (d, J=6.6 Hz, 1H)

LRMS (FAB, NBA matrix) m/z319 [(M+H)$^+$; calcd for $C_{14}H_{27}N_2O_4S$:319]

EXAMPLE 19

β-lactone (10 mg, 0.047 mmol), obtained by the method of Referential Example 2 was dissolved in dichloromethane (1.0 ml), under an argon atmosphere. Triethylamine (6 eq., 0.0282 mmol, 39.3 μl), and mercapto acetic acid (3 eq., 0.141 mmol, 12.9 mg), were added thereto. The reaction mixture was stirred at 50° C. for 1 hour, concentrated in vacuo and purified using preparative TLC (developer, CHCl$_3$:MeOH=3:1), to obtain 3-hydroxy-2-(1-hydroxy-2-methylpropyl)-4-methyl-5-oxo-2-pyrrolidine-1-carboxymethylthiocarboxylate 8.6 mg (yield:60%).

$^1$H-NMR (270 MHz, CDCl$_3$) δ 0.79 (d, J=6.6H, 3H), 0.87 (d, J=6.6 Hz, 3H), 0.98 (d, J=7.6 Hz, 3H), 1.58 (m, 1H), 2.83 (m, 1H), 3.50 (s, 2H), 3.86 (d, J=6.9 Hz, 1H), 4.43 (d, J=6.6 Hz, 1H)

LRMS (FAB, NBA matrix) m/z306 [(M+H)$^+$; calcd for C$_{12}$H$_{20}$NO$_6$S:306]

EXAMPLE 20

β-lactone (10 mg, 0.047 mmol), obtained by the method of Referential Example 2 was dissolved in dichloromethane (1.0 ml), under an argon atmosphere. Triethylamine (6 eq., 0.0282 mmol, 39.3 μl), and methylthioglycolate (3 eq., 0.141 mmol, 15.0 mg), were added thereto. The reaction mixture was stirred at 40° C. for 2 hours, concentrated in vacuo and purified using preparative TLC (developer, CHCl$_3$:MeOH=10:1), to obtain 3-hydroxy-2-(1-hydroxy-2-methylpropyl)-4-methyl-5-oxo-2-pyrrolidine-methoxycarbonylthiocarboxylate 12.7 mg (yield:85%).

$^1$H-NMR (270 MHz, CDCl$_3$) δ 0.79 (d, J=6.6H, 3H), 0.87 (d, J=6.61 Hz, 3H), 0.98 (d, J=7.6 Hz, 3H), 1.58 (m, 1H), 2.83 (m, 1H), 3.35 (s, 3H), 3.50 (s, 2H), 3.86 (d, J=6.9 Hz, 1H) 4.43 (d, J=6.6 Hz, 1H)

LRMS (FAB, NBA matrix) m/z320 [(M+H)$^+$; calcd for C$_{13}$H$_{22}$NO$_6$S:320]

EXAMPLE 21

β-lactone (10 mg, 0.047 mmol), obtained by the method of Referential Example 2 was dissolved in dichloromethane (1.0 ml), under an argon atmosphere. Triethylamine (6 eq., 0.0282 mmol, 39.3 μl), and methyl-3-mercapto propionate (3 eq., 0.141 mmol, 15.6 μl), were added thereto. The reaction mixture was stirred at 40° C. for 1 hour, concentrated in vacuo and purified using preparative TLC (developer, CHCl$_3$:MeOH=20:1), to obtain 3-hydroxy-2-(1-hydroxy-2-methylpropyl)-4-methyl-5-oxo- 2-pyrrolidine-methoxycarbonylethylthiocarboxylate 11.7 mg (yield:75%).

$^1$H-NMR (270 MHz, CDCl$_3$) δ 0.79 (d, J=6.6H, 3H), 0.87 (d, J=6.6 Hz, 3H), 0.98 (d, J=7.6 Hz, 3H), 1.58 (m, 1H), 2.23 (m, 2H), 2.83 (m, 1H), 3.35 (s, 3H), 3.19 (m, 2H), 3.86 (d, J=6.9 Hz, 1H), 4.43 (d, J=6.6 Hz, 1H)

LRMS (FAB, NBA matrix) m/z334 [(M+H)$^+$; calcd for C$_{14}$H$_{24}$NO$_6$S:334]

EXAMPLE 22

β-lactone (10 mg, 0.047 mmol), obtained by the method of Referential Example 2 was dissolved in dichloromethane (1.0 ml), under an argon atmosphere. Triethylamine (6 eq., 0.0282 mmol, 39.3 μl), and 2-mercapto pyridine (6 eq., 0.282 mmol, 29.2 mg), were added thereto. The reaction mixture was stirred at 40° C. for 1 hour, concentrated in vacuo and purified using preparative TLC (developer, CHCl$_3$:MeOH=10:1), to obtain 3-hydroxy-2-(1-hydroxy-2-methylpropyl)-4-methyl-5-oxo-2-pyrrolidine-2-pyridylthiocarboxylate 14.0 mg (yield:92%).

$^1$H-NMR (270 MHz, CDCl$_3$) δ 0.79 (d, J=6.6H, 3H), 0.87 (d, J=6.6 Hz, 3H), 0.98 (d, J=7.6 Hz, 3H), 1.58 (m, 1H), 2.83 (m, 1H), 3.86 (d. J=6.9 Hz, 1H), 4.43 (d, J=6.6 Hz, 1H), 7.30~8.2 (m, 4H)

LRMS (FAB, NBA matrix) m/z325 [(M+H)$^+$; calcd for C$_{15}$H$_{21}$N$_2$O$_4$S:325]

EXAMPLE 23

β-lactone (10 mg, 0.047 mmol), obtained by the method of Referential Example 2 was dissolved in dichloromethane (1.0 ml), under an argon atmosphere. Triethylamine (6 eq., 0.0282 mmol, 39.3 μl), and 2-mercapto pyridine (6 eq., 0.282 mmol, 29.2 mg), were added thereto. The reaction mixture was stirred at 40° C. for 8 hours, concentrated in vacuo and purified using preparative TLC (developer, CHCl$_3$:MeOH=10:1), to obtain 3-hydroxy-2-(1-hydroxy-2-methylpropyl)-4-methyl-5-oxo-2-pyrrolidine-4-pyridylthiocarboxylate 9.9 mg (yield:65%).

$^1$H-NMR (270 MHz, CDCl$_3$) δ 0.79 (d, J=6.6H, 3H), 0.87 (d, J=6.6 Hz, 3H), 0.98 (d, J=7.6 Hz, 3H), 1.58 (m, 1H), 2.83 (m, 1H), 3.86 (d, J=6.9 Hz, 1H), 4.43 (d, J=6.6 Hz, 1H), 7.30~8.2 (m, 4H)

LRMS (FAB, NBA matrix) m/z325 [(M+H)$^+$; calcd for C$_{15}$H$_{21}$N$_2$O$_4$S:325]

EXAMPLE 24

β-lactone (10 mg, 0.047 mmol), obtained by the method of Referential Example 2 was dissolved in dichloromethane (1.0 ml), under an argon atmosphere. Triethylamine (6 eq., 0.0282 mmol, 39.3 μl), and homocysteine (6 eq., 0.282 mmol, 38.1 mg), were added thereto. The reaction mixture was stirred at 40° C. for 15 hours, concentrated in vacuo and purified using preparative TLC (developer, CHCl$_3$:MeOH= 3:1), to obtain 3-hydroxy-2-( 1-hydroxy-2-methylpropyl)-4-methyl-5-oxo-2-pyrrolidinecarboxylate 7.5 mg (yield:45%).

$^1$H-NMR (270 MHz, CDCl$_3$) δ 0.79 (d, J=6.6H, 3H), 0.87 (d, J=6.6 Hz, 3H), 0.98 (d, J=7.6 Hz, 3H), 1.58 (m, 1H), 1.83 (m, 2.52 (m, 2H), 2.83 (m, 1H), 3.86 (d, J=6.9 Hz, 1H), 4.43 (d, J=6.6 Hz, 1H), 4.55 (m, 1H), 8.00 (bs, 1H)

LRMS (FAB, NBA matrix) m/z349 [(M+H)$^+$; calcd for C$_{14}$H$_{25}$N$_2$O$_6$S:349]

EXAMPLE 25

β-lactone (10 mg, 0.047 mmol), obtained by the method of Referential Example 2 was dissolved in dichloromethane (1.0 ml), under an argon atmosphere. Triethylamine (6 eq., 0.0282 mmol, 39.3 μl), and N-(2-mercapto-propionyl), glycine (3 eq., 0.141 mmol, 51.0 mg), were added thereto. The reaction mixture was stirred at 40° C. for 15 hours, concentrated in vacuo and purified using preparative TLC (developer, CHCl$_3$:MeOH=3:1), to obtain 2-S-propionylglycine-3-hydroxy-2-(1-hydroxy-2-methylpropyl)-4-methyl-5-oxo-2-pyrrolidinecarboxylate 5.3 mg (yield:30%).

$^1$H-NMR (270 MHz, CDCl$_3$) δ 0.79 (d, J=6.6H, 3H), 0.87 (d, J=6.6 Hz, 3H), 0.98 (d, J=7.6 Hz, 3H), 1.35 (d, 3H), 1.58 (m, 1H), 1.83 (m, 2H), 2.52 (m, 2H), 2.73 (m, 1H), 2.83 (m, 1H), 3.86 (d, J=6.9 Hz, 1H), 4.22 (m, 1H), 4.43 (d, J=6.6 Hz, 1H), 4.55 (m, 1H), 8.00 (bs. 1H)

LRMS (FAB, NBA matrix) m/z377 [(M+H)$^+$; calcd for C$_{15}$H$_{25}$N$_2$O$_7$S:377]

EXAMPLE 26

β-lactone (20 mg, 0.094 mmol), obtained by the method of Referential Example 2 was dissolved in dichloromethane (1.0 ml), under an argon atmosphere. Triethylamine (12 eq., 0.0564 mmol, 78.6 μl), and reduced glutathione (3 eq., 0.282 mmol, 87.0 mg), were added thereto. The reaction mixture was stirred at 40° C. for 36 hours, concentrated in vacuo and purified using preparative TLC (developer, CHCl$_3$:MeOH= 2:1), to obtain glutathione-3-hydroxy-2-(1-hydroxy-2-methylpropyl)-4-methyl-5-oxo-2-pyrrolidinethiocarboxylate 7.3 mg (yield:15%).

$^1$H-NMR (270 MHz, CDCl$_3$) δ 0.79 (d, J=6.6H, 3H), 0.87 (d, J=6.6 Hz, 3H), 0.98 (d, J=7.6 Hz, 3H), 1.50 (m, 2H), 1.58 (m, 1H), 2.72 (m, 2H), 2.83 (m, 1H), 3.10 (m, 2H), 3.70 (s, 2H), 3.86 (d, J=6.9 Hz, 1H), 4.43 (d, J=6.6 Hz, 1H), 4.55 (m, 1H), 4.75 (m, 1H), 8.00 (bs, 1H)

LRMS (FAB, NBA matrix) m/z521 [(M+H)$^+$; calcd for C$_{20}$H$_{33}$N$_4$O$_{10}$S:521]

We claim:

1. A lactacystin derivative other than lactacystin, of the formula

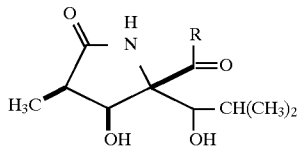

wherein R is lower alkoxy, —S—(CH$_2$)$_n$R$^1$ or —S—(CH$_2$)$_n$—CH(R$^2$)-(R$^3$), in which R$^1$ is branched or straight-chain lower alkyl, hydroxy, carboxyl, lower alkoxycarbonyl, optionally substituted phenyl, substituted or unsubstituted amino or pyridyl, R$^2$ is substituted or unsubstituted amino, lower alkyl or amino acid residue, R$^3$ is carboxyl, lower alkoxycarbonyl, or amino acid residue, and n is 0–4, or a pharmacologically acceptable salt thereof with the proviso that when n is 1, 2 or 3, R$^1$ is not acetylamino; and when n is 1 and one of R$^2$ and R$^3$ is COOH, the other of R$^2$ and R$^3$ is not acetylamino or phenylacetylamino.

2. A lactacystin derivative according to claim 1, which is τ-lactam methyl ester or a pharmacologically acceptable salt thereof.

3. A lactacystin derivative according to claim 1, which is des-N-acetylamino lactacystin or a pharmacologically acceptable salt thereof.

4. A lactacystin derivative according to claim 1, which is des-N-acetylamino lactacystin ethyl ester or a pharmacologically acceptable salt thereof.

5. A lactacystin derivative according to claim 1, which is des-N-acetyl descarboxy lactacystin or a pharmacologically acceptable salt thereof.

6. A lactacystin derivative according to claim 1, which is lactacystin methyl ester or a pharmacologically acceptable salt thereof.

7. A lactacystin derivative according to claim 1, which is 3-hydroxy-2-(1-hydroxy-2-methylpropyl)-4-methyl-5-oxo-2-pyrrolidine-ethanethiocarboxylate or a pharmacologically acceptable salt thereof.

8. A lactacystin derivative according to claim 1, which is 3-hydroxy-2-(1-hydroxy-2-methylpropyl)-4-methyl-5-oxo-2-pyrrolidine-propanethiocarboxylate or a pharmacologically acceptable salt thereof.

9. A lactacystin derivative according to claim 1, which is 3-hydroxy-2-(1-hydroxy-2-methylpropyl)-4-methyl-5-oxo-2-pyrrolidine-iso-propanethiocarboxylate or a pharmacologically acceptable salt thereof.

10. A lactacystin derivative according to claim 1, which is 3-hydroxy-2-(1-hydroxy-2-methylpropyl)-4-methyl-5-oxo-2-pyrrolidine-butanethiocarboxylate or a pharmacologically acceptable salt thereof.

11. A lactacystin derivative according to claim 1, which is 3-hydroxy-2-(1-hydroxy-2-methylpropyl)-4-methyl-5-oxo-2-pyrrolidine-1-methyl-1-propanethiocarboxylate or a pharmacologically acceptable salt thereof.

12. A lactacystin derivative according to claim 1, which is 3-hydroxy-2-(1-hydroxy-2-methylpropyl)-4-methyl-5-oxo-2-pyrrolidine-1-pentanethiocarboxylate or a pharmacologically acceptable salt thereof.

13. A lactacystin derivative according to claim 1, which is 3-hydroxy-2-(1-hydroxy-2-methylpropyl)-4-methyl-5-oxo-2-pyrrolidine-phenylthiocarboxylate or a pharmacologically acceptable salt thereof.

14. A lactacystin derivative according to claim 1, which is 3-hydroxy-2-(1-hydroxy-2-methylpropyl)-4-methyl-5-oxo-2-pyrrolidine-2-hydroxyethanethiocarboxylate or a pharmacologically acceptable salt thereof.

15. A lactacystin derivative according to claim 1, which is 3-hydroxy-2-(1-hydroxy-2-methylpropyl)-4-methyl-5-oxo-2-pyrrolidine-3-hydroxypropanethiocarboxylate or a pharmacologically acceptable salt thereof.

16. A lactacystin derivative according to claim 1, which is 3-hydroxy-2-(1-hydroxy-2-methylpropyl)-4-methyl-5-oxo-2-pyrrolidine-4-hydroxyphenylthiocarboxylate or a pharmacologically acceptable salt thereof.

17. A lactacystin derivative according to claim 1, which is 3-hydroxy-2-(1-hydroxy-2-methylpropyl)-4-methyl-5-oxo-2-pyrrolidine-2-N-methyl-ethanethiocarboxylate or a pharmacologically acceptable salt thereof.

18. A lactacystin derivative according to claim 1, which is 3-hydroxy-2-(1-hydroxy-2-methylpropyl)-4-methyl-5-oxo-2-pyrrolidine-2-N-dimethyl-ethanethiocarboxylate or a pharmacologically acceptable salt thereof.

19. A lactacystin derivative according to claim 1, which is 3-hydroxy-2-(1-hydroxy-2-methylpropyl)-4-methyl-5-oxo-2-pyrrolidine-1-carboxymethylthiocarboxylate or a pharmacologically acceptable salt thereof.

20. A lactacystin derivative according to claim 1, which is 3-hydroxy-2-(1-hydroxy-2-methylpropyl)-4-methyl-5-oxo-2-pyrrolidine-methoxycarbonylmethylthiocarboxylate or a pharmacologically acceptable salt thereof.

21. A lactacystin derivative according to claim 1, which is 3-hydroxy-2-(1-hydroxy-2-methylpropyl)-4-methyl-5-oxo-2-pyrrolidine-methoxycarbonylethylthiocarboxylate or a pharmacologically acceptable salt thereof.

22. A lactacystin derivative according to claim 1, which is 3-hydroxy-2-(1-hydroxy-2-methylpropyl)-4-methyl-5-oxo-2-pyrrolidine-2-pyridylthiocarboxylate or a pharmacologically acceptable salt thereof.

23. A lactacystin derivative according to claim 1, which is 3-hydroxy-2-(1-hydroxy-2-methylpropyl)-4-methyl-5-oxo-2-pyrrolidine-4-pyridylthiocarboxylate or a pharmacologically acceptable salt thereof.

24. A lactacystin derivative according to claim 1, which is homocysteine-3-hydroxy-2-(1-hydroxy-2-methylpropyl)-4-methyl-5-oxo-2-pyrrolidine-carboxylate or a pharmacologically acceptable salt thereof.

25. A lactacystin derivative according to claim 1, which is 2-S-propionylglycine-3-hydroxy-2-(1-hydroxy-2-methylpropyl)-4-methyl-5-oxo-2-pyrrolidinecarboxylate or a pharmacologically acceptable salt thereof.

26. A lactacystin derivative according to claim 1, which is glutathione-3-hydroxy-2-(1-hydroxy-2-methylpropyl)-4-methyl-5-oxo-2-pyrrolidinethiocarboxylate or a pharmacologically acceptable salt thereof.

\* \* \* \* \*